(12) United States Patent
Chang et al.

(10) Patent No.: US 12,036,559 B2
(45) Date of Patent: *Jul. 16, 2024

(54) MOLECULAR DIAGNOSTICS APPARATUS

(71) Applicant: Wistron Corp., New Taipei (TW)

(72) Inventors: Yao-Tsung Chang, New Taipei (TW); Wen-Hui Shih, New Taipei (TW); Chen An Sung, New Taipei (TW)

(73) Assignee: WISTRON CORP., New Taipei (TW)

( * ) Notice: Subject to any disclaimer, the term of this patent is extended or adjusted under 35 U.S.C. 154(b) by 1079 days.

This patent is subject to a terminal disclaimer.

(21) Appl. No.: 16/892,247

(22) Filed: Jun. 3, 2020

(65) Prior Publication Data
US 2021/0154675 A1   May 27, 2021

(30) Foreign Application Priority Data
Nov. 26, 2019  (TW) .................. 108215636

(51) Int. Cl.
*B01L 3/00*   (2006.01)
*B01L 7/00*   (2006.01)
*C12Q 1/686*   (2018.01)

(52) U.S. Cl.
CPC ............. *B01L 7/52* (2013.01); *C12Q 1/686* (2013.01); *B01L 2200/147* (2013.01); *B01L 2300/1894* (2013.01); *C12Q 2561/113* (2013.01)

(58) Field of Classification Search
CPC ......... B01L 2200/147; B01L 2300/023; B01L 2300/0803; B01L 2300/1816; B01L 2300/1822; B01L 2300/1844; B01L 2300/1894; B01L 7/52; C12Q 1/686; C12Q 2561/113; G05D 23/192
See application file for complete search history.

(56) References Cited

U.S. PATENT DOCUMENTS

2007/0095393 A1* 5/2007 Zucchelli .......... B01L 3/502738
                                                              137/68.11
2013/0157276 A1* 6/2013 Edvinsson ............. C12Q 1/686
                                                                435/6.12

FOREIGN PATENT DOCUMENTS

| CN | 105071553 A | 11/2015 |
|---|---|---|
| CN | 108107024 A | 6/2018 |
| CN | 108962533 A | 12/2018 |
| TW | I470899 B | 1/2015 |
| TW | 201617600 A | 5/2016 |
| TW | 201743537 A | 12/2017 |

* cited by examiner

*Primary Examiner* — Lydia Edwards

(57) ABSTRACT

A molecular diagnostics apparatus which is adapted to perform DNA chain replication to one sample is provided, including a bracket, a central control module, a central control module coil, a rotational carrier, a detection module and a detection module coil. The central control module is disposed on the bracket. The central control module coil is coupled to the central control module. The rotational carrier is adapted to be rotated relative to the bracket, wherein the sample is disposed on the rotational carrier. The detection module is disposed on the rotational carrier. The detection module coil is coupled to the detection module. In a charging mode, the central control module makes the central control module coil provide an induced electromotive force. The detection module coil generates an induced current according to the induced electromotive force. The induced current is supplied to the detection module.

15 Claims, 21 Drawing Sheets

MOLECULAR DIAGNOSTICS APPARATUS

CROSS REFERENCE TO RELATED APPLICATIONS

This application claims priority of Taiwan Patent Application No. 108215636, filed on Nov. 26, 2019, the entirety of which is incorporated by reference herein.

BACKGROUND OF THE INVENTION

Field of the Invention

The present invention relates to a molecular diagnostics apparatus, and in particular to a molecular diagnostics apparatus with wireless power supply function.

Description of the Related Art

Polymerase chain reaction (PCR) is a method widely used in molecular biology to rapidly make millions to billions of copies of a specific DNA sample allowing scientists to take a very small sample of DNA and amplify it to a large enough amount to study in detail. Real-Time PCR (quantitative-PCR, q-PCR) can monitor the entire polymerase chain reaction in real time. The polymerase chain reaction mainly includes a temperature control part and a detection part. The temperature control part provides the temperature cycling required for the polymerase chain reaction. The detection part uses a specific excitation wavelength to make the fluorescence dye emit a fluorescence signal. An optical sensor and a filter are then utilized to capture and detect a specific wavelength band. Performing a polymerase chain reaction once can get about 2 times the DNA amplified products. After performing N times, about $2^N$ DNA amplified products can be obtained. When the DNA amplified product doubles, the fluorescence signal gradually increases and accumulates. Therefore, real-time PCR (q-PCR) can be used to monitor the temperature and fluorescence changes of the entire polymerase chain reaction in real time, to record the number of cycles and fluorescence intensity changes, and to quantitatively analyze the DNA concentration.

Conventionally, the molecular diagnostics apparatus has a rotational carrier and a temperature detection module. The temperature detection module is disposed on the rotational carrier. The temperature data provided by the temperature detection module and the required power are transmitted by a signal-cable and a power-cable. One end of the signal-cable/power-cable is connected to a fixed central control module, and the other end of the signal-cable/power-cable is connected to the rotating temperature detection module. Therefore, the reliability of the signal-cable/power-cable is low, and the overall mechanism design of the molecular diagnostics apparatus is complicated.

BRIEF SUMMARY OF THE INVENTION

Embodiments of the inventions are provided to solve the aforementioned difficulty.

In one embodiment, a molecular diagnostics apparatus is provided. The molecular diagnostics apparatus is adapted to perform DNA chain replication to one sample. The molecular diagnostics apparatus includes a bracket, a central control module, a central control module coil, a rotational carrier, a detection module and a detection module coil. The central control module is disposed on the bracket. The central control module coil is coupled to the central control module. The rotational carrier is adapted to be rotated relative to the bracket. The sample is disposed on the rotational carrier. The detection module is disposed on the rotational carrier. The detection module coil is coupled to the detection module. In a charging mode, the central control module makes the central control module coil provide an induced electromotive force (electromagnetic field), the detection module coil generates an induced current according to the induced electromotive force (electromagnetic field), and the induced current is supplied to the detection module.

Utilizing the molecular diagnostics apparatus of the embodiment of the invention, the structure of the molecular diagnostics apparatus can be simplified by the wireless power supply design and the wireless data transmission design. The reliability of the signal transmission and power transmission can be improved.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1A:
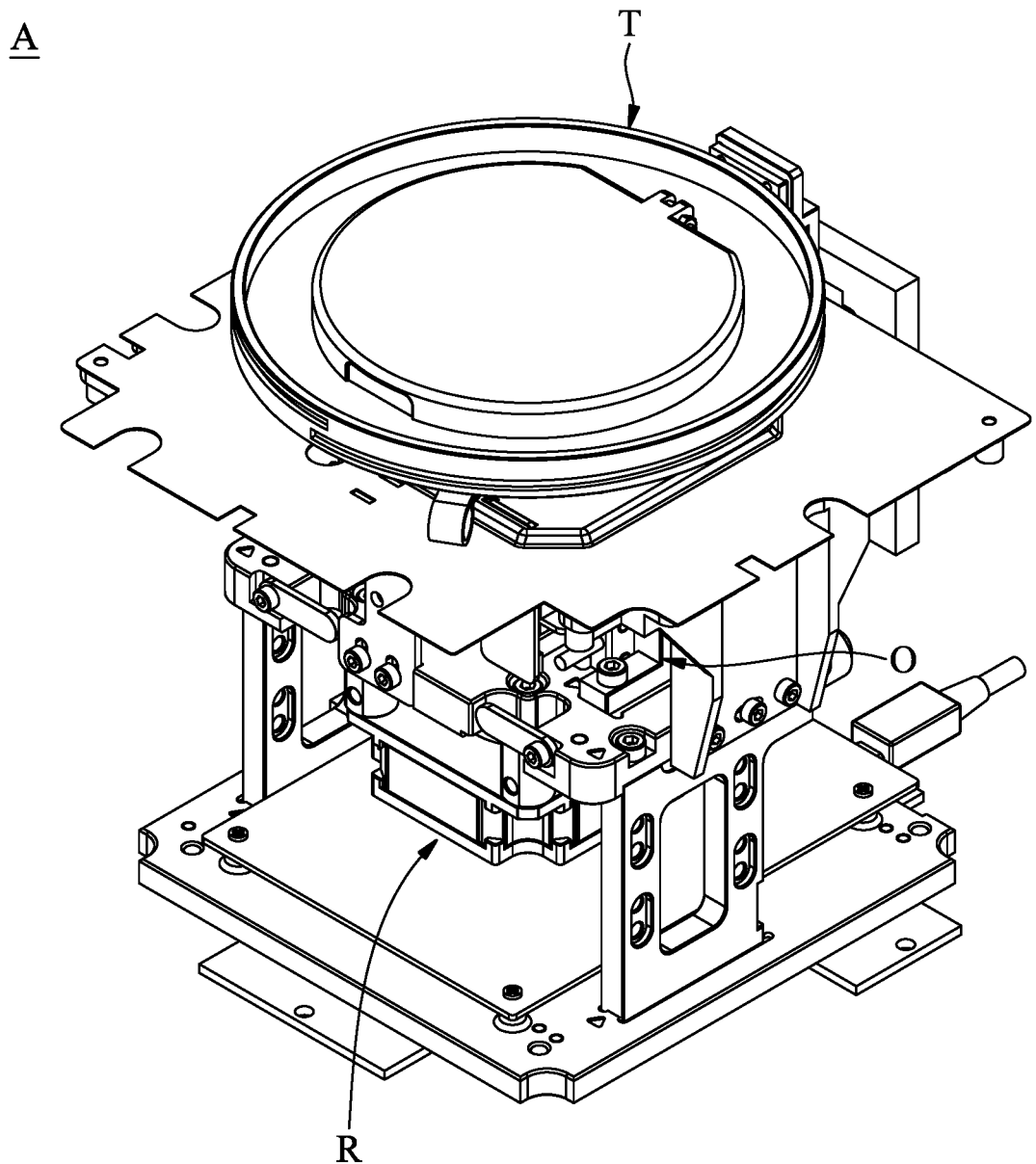
FIG. 1A is an assembled view of a molecular diagnostics apparatus of the embodiment of the invention.
Figure 1B:
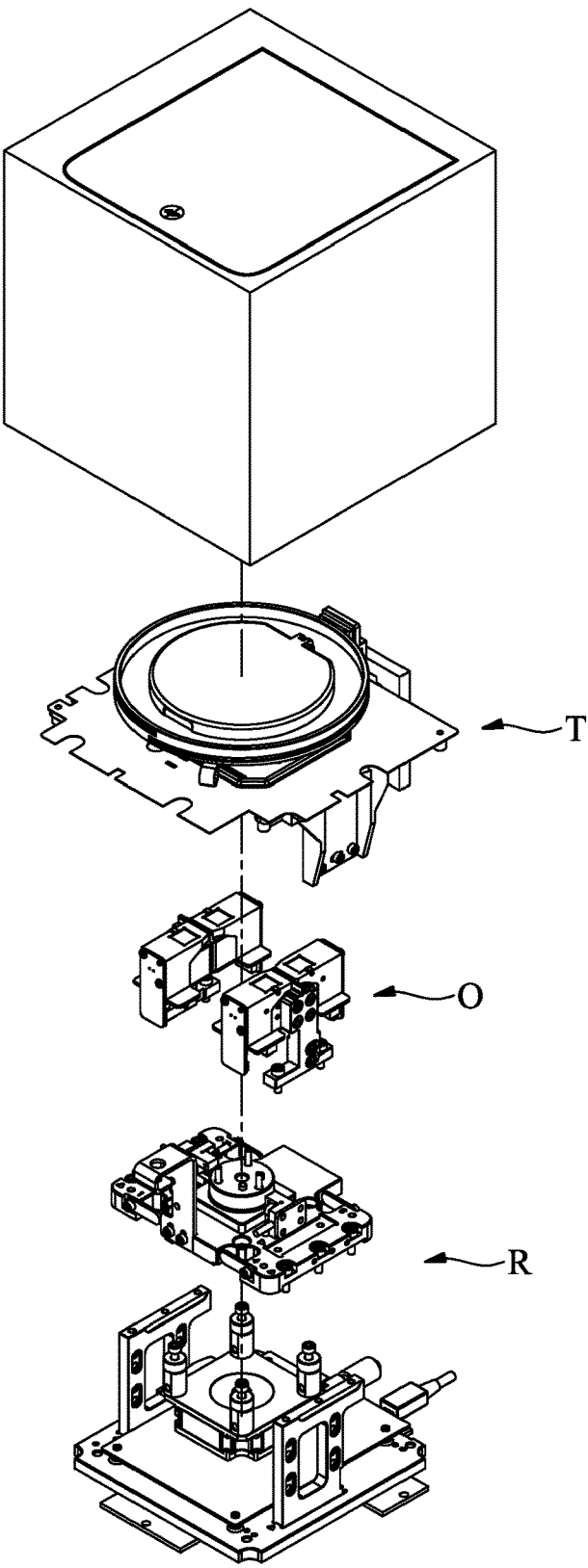
FIG. 1B is an exploded view of the molecular diagnostics apparatus of the embodiment of the invention.

FIG. 1A is an assembled view of a molecular diagnostics apparatus of the embodiment of the invention. FIG. 1B is an exploded view of the molecular diagnostics apparatus of the embodiment of the invention. With reference to FIGS. 1A and 1B, in one embodiment, the molecular diagnostics apparatus A of the embodiment of the invention is a real-time polymerase chain reaction (qPCR) apparatus. The molecular diagnostics apparatus A includes a temperature control system T, an optical system O and a rotation system R. The temperature control system T provides the three-stage temperature cycle required for the polymerase chain reaction thermal cycle to the test tube containing the fluorescence dye. The process of polymerase chain reaction must include a denaturation step whose temperature is raised to 94° C., an annealing step whose temperature is decreased to 50° C.~60° C., and an extension step whose temperature is raised to 72° C. The optical system O captures data and analyzes the fluorescence signal excited by the fluorescence dye in the test tube after each thermal cycle. The rotation system R utilizes a motor to rotate the turntable of the temperature control system (in one embodiment, the turntable carries sixteen test tubes). Therefore, the sixteen test tubes containing fluorescence dye can correspond to different optical system positions. The specific excitation wavelength of the optical system O causes the fluorescence dye to generate a fluorescent signal. Then, a photodiode of the optical system O captures the fluorescence brightness and analyzes the final DNA concentration. The above temperature values can be adjusted according to different DNA sequence and different reagents/dyes.

Figure 2A:
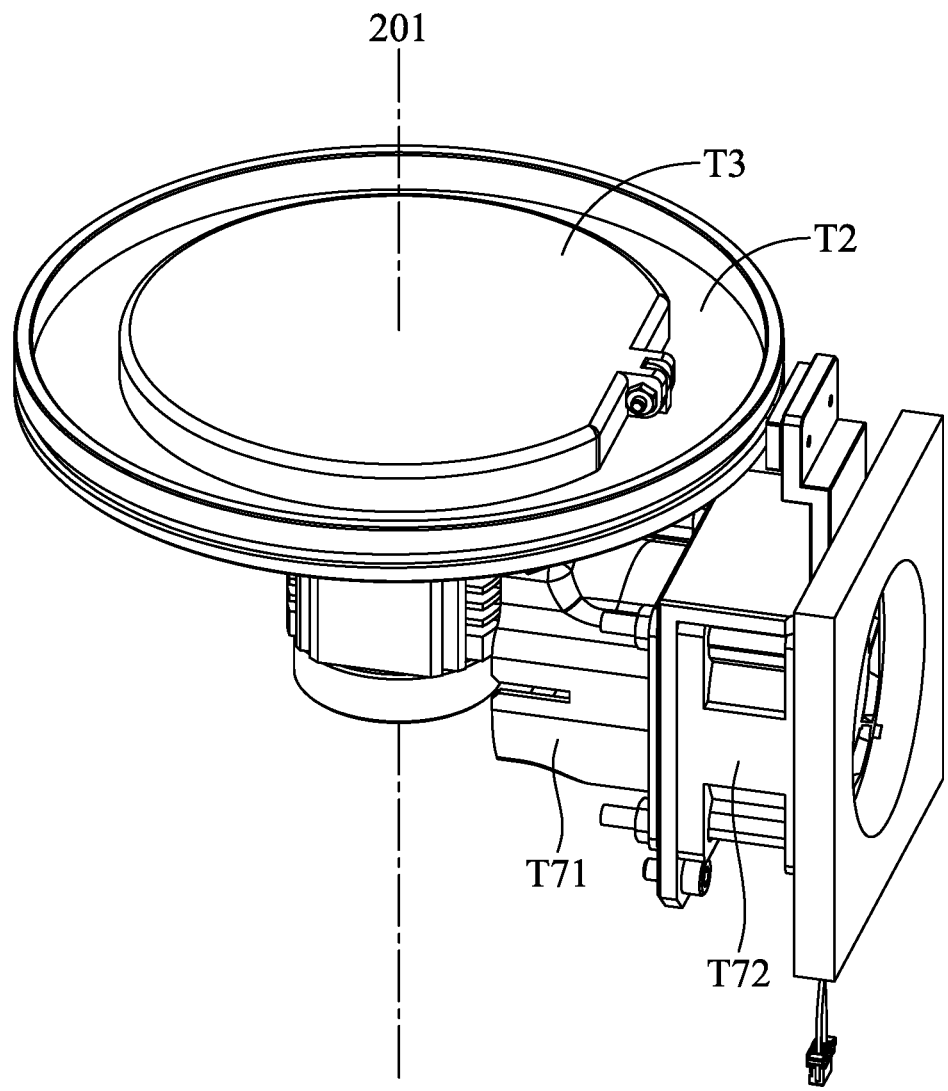
FIGS. 2A and 2B show details of a temperature control system of the embodiment of the invention.
Figure 2B:
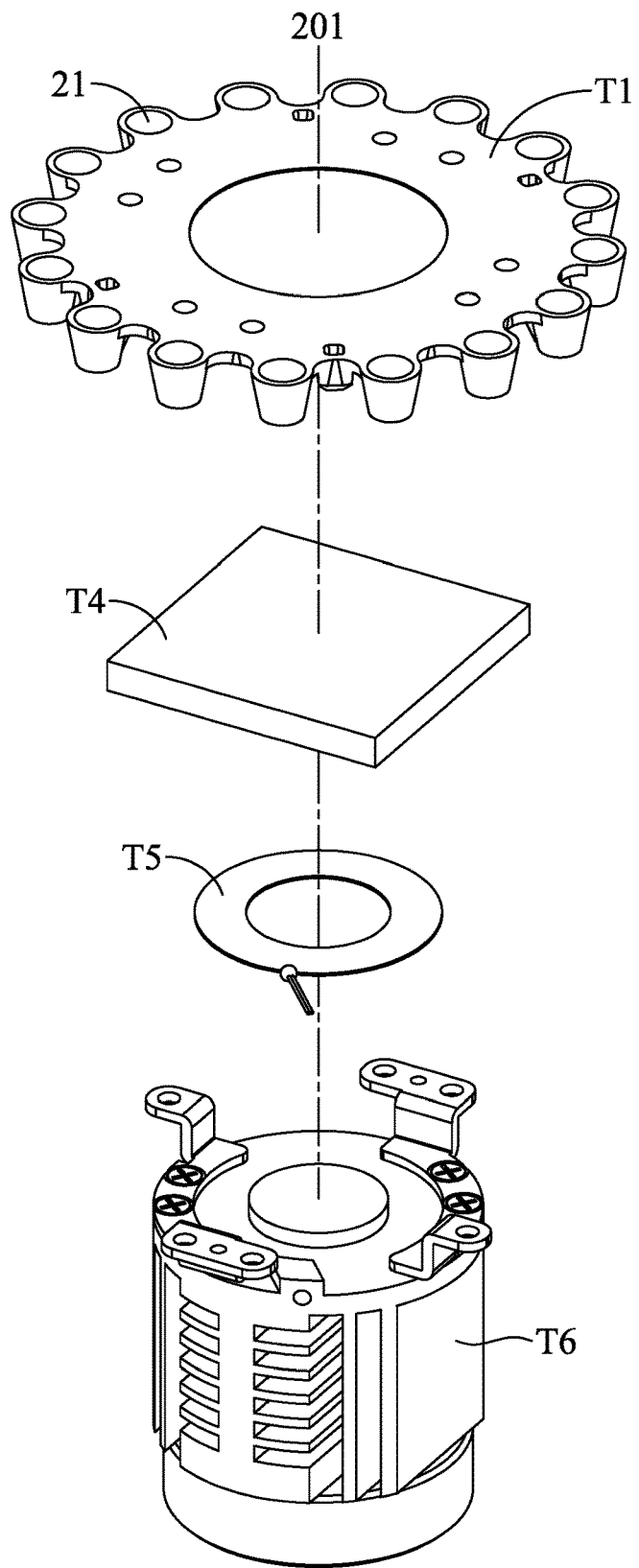
Figure 2C:
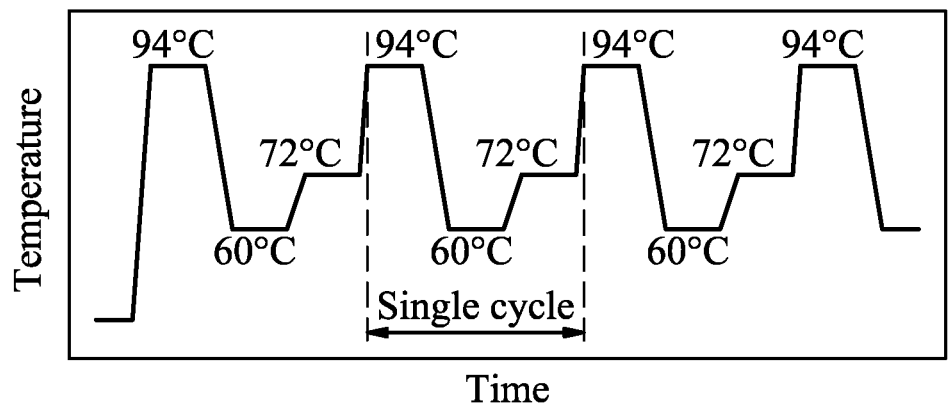
FIG. 2C shows the temperature of the three-stage temperature cycle required for the polymerase chain reaction of the embodiment of the invention.

FIGS. 2A and 2B show details of the temperature control system of the embodiment of the invention. With reference to FIGS. 2A and 2B, the temperature control system T of the embodiment of the invention utilizes a thermoelectric cooling chip (TEC) for heating and cooling to make the temperature rise and fall rapidly. The temperature control system T includes a heating block T1, a holder T2, a cover T3, a thermoelectric cooling chip T4, a heater T5, a heat sink T6, a fan duct T71 and a fan T72. Heating block T1 is used to place the test tube. The holder T2 is used to prevent the test tube from tilting. The cover T3 is used to apply pressure to bring the test tube into contact with the heating block T1. The thermoelectric cooling chip (TEC) T4 is used to precisely adjust the temperature rise and fall with the heater T5, the heat sink T6, the fan duct T71 and the fan T72. The temperature of the three-stage temperature cycle required for the polymerase chain reaction is shown in FIG. 2C. At the beginning, the denaturation step is performed, and the temperature is increased to the first stage temperature of 94° C. The hot end of the thermoelectric cooling chip T4 contacts the heating block T1 to raise the temperature of the heating block T1. At this time, the heater T5 is turned on and heats the heating block T1 with the thermoelectric cooling chip T4. A computer program is used to control and maintain the temperature of the first stage of the polymerase chain reaction. Another function of the heater T5 is to maintain the temperature difference between the two ends of the thermoelectric cooling chip T4 at a certain value, so as to maintain the heating rate. Then, the annealing step is performed, and the temperature is decreased to the second stage temperature of 55° C.~60° C. At this time, the voltage applied to the thermoelectric cooling chip T4 is reversed, and the cold and hot ends are switched. The heater T5 is turned off and the fan T72 is turned on. The heat sink T6 conducts the heat from the hot end of the thermoelectric cooling chip T4. The fan T72 forces convection to export the heat outside the apparatus and adjust the temperature precisely with the temperature difference between the two ends of the thermoelectric cooling chip T4. Finally, the extension step is performed, and the temperature is raised to the third stage temperature of 72° C.

Figure 3:
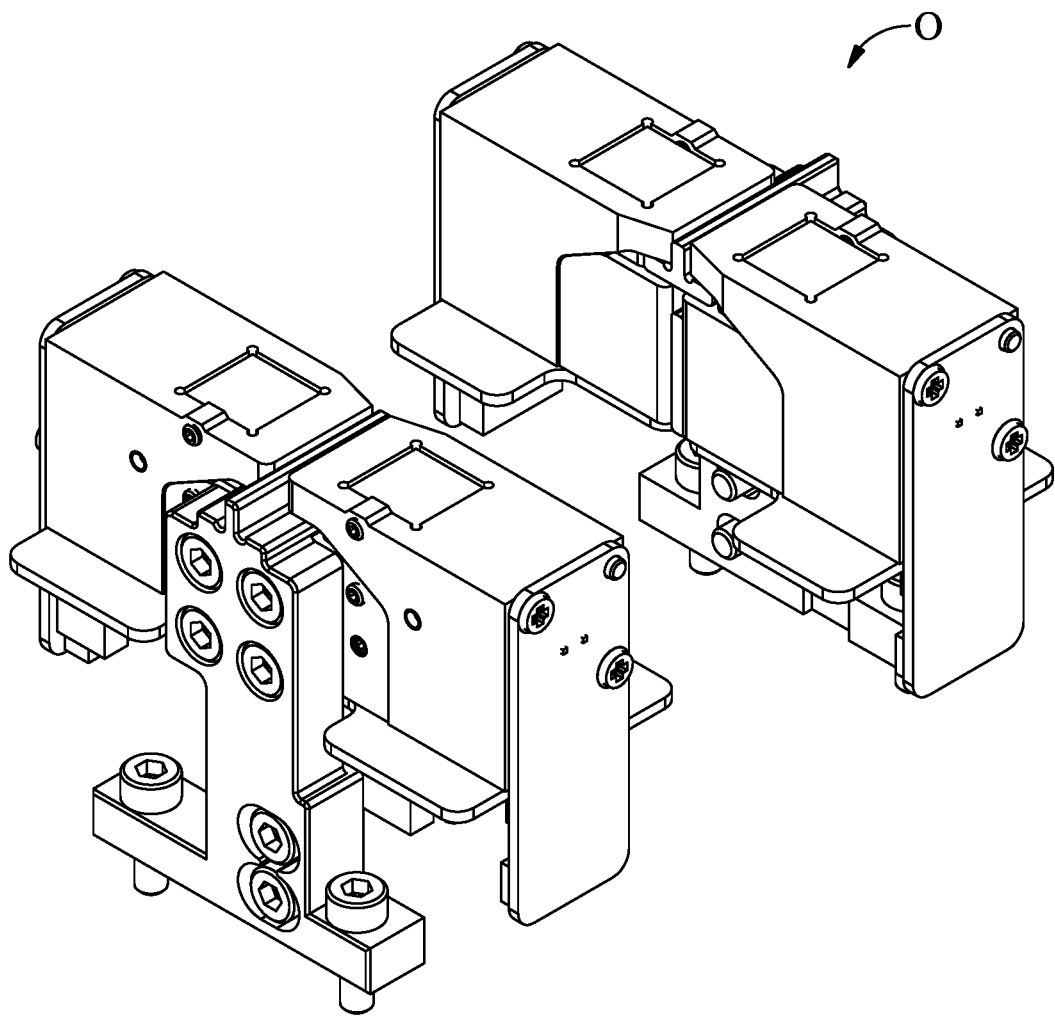
FIG. 3 shows details of an optical system of the embodiment of the invention.

FIG. 3 shows details of the optical system of the embodiment of the invention. With reference to FIG. 3, in one embodiment of the invention, the optical system O has four optical devices. Each optical device includes an excitation filter, a dichroic filter, an emission filter, and a photodiode. In one embodiment, the aforementioned optical device can be used to detect four kinds of specific fluorescence dyes: green (excitation peak at 494 nm, emission peak at 520 nm), yellow (excitation peak at 550 nm, emission peak at 570 nm), orange (excitation peak at 575 nm, emission peak at 602 nm), and red (excitation peak at 646 nm, emission peak at 662 nm).

As to the details of the optical device, in the optical device, the light emitted by the monochromatic light-emitting diode (LED) passes through the excitation filter, and is reflected by the dichroic filter (the dichroic filter can reflect the short wave and allow the long wave to pass), and shines upward toward the bottom of the test tube containing the fluorescence dye. After the fluorescence dye is excited, the fluorescent light passes through the dichroic filter and the emission filter. After filtering out all unwanted noise light sources, it is received by a photodiode. After a series of light paths, the final change in fluorescence characteristics is observed for analysis.

Figure 4:
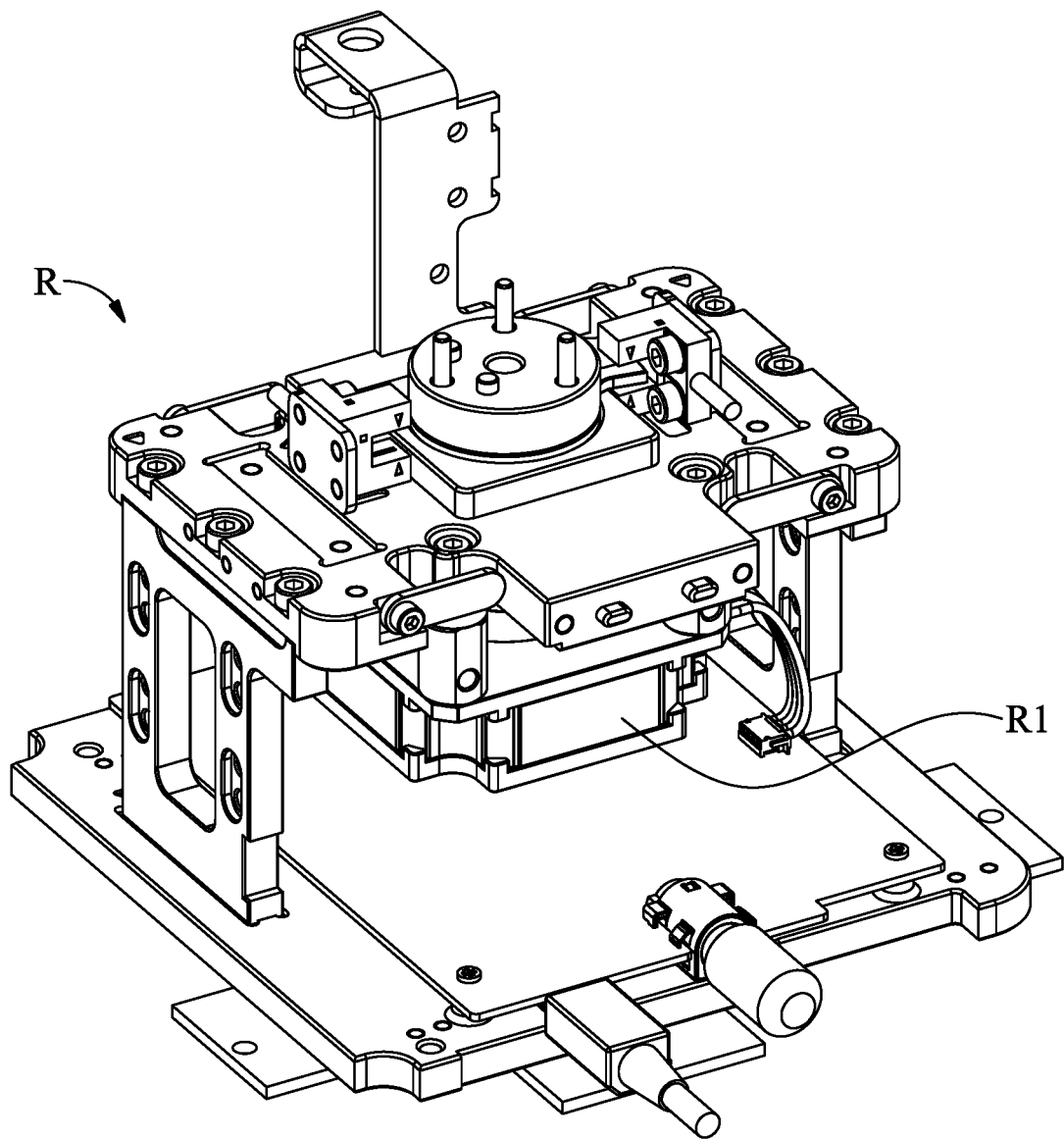
FIG. 4 shows a rotation system of the embodiment of the invention.

FIG. 4 shows the rotation system of the embodiment of the invention. With reference to FIG. 4, the motor R1 of the rotation system R directly rotates the temperature control system T, so that the test tubes containing the fluorescence dye on the temperature control system T can correspond to the positions of the four optical devices for being detected. In an embodiment, the rotation system R may include a limit sensor, which detects the initial point (Home) and the stopping point (End) in the rotation position of the motor R1 by using a light interruption method. The molecular diagnostics apparatus differentiates the test tube through the collaboration of the firmware and the software.

Figure 5A:
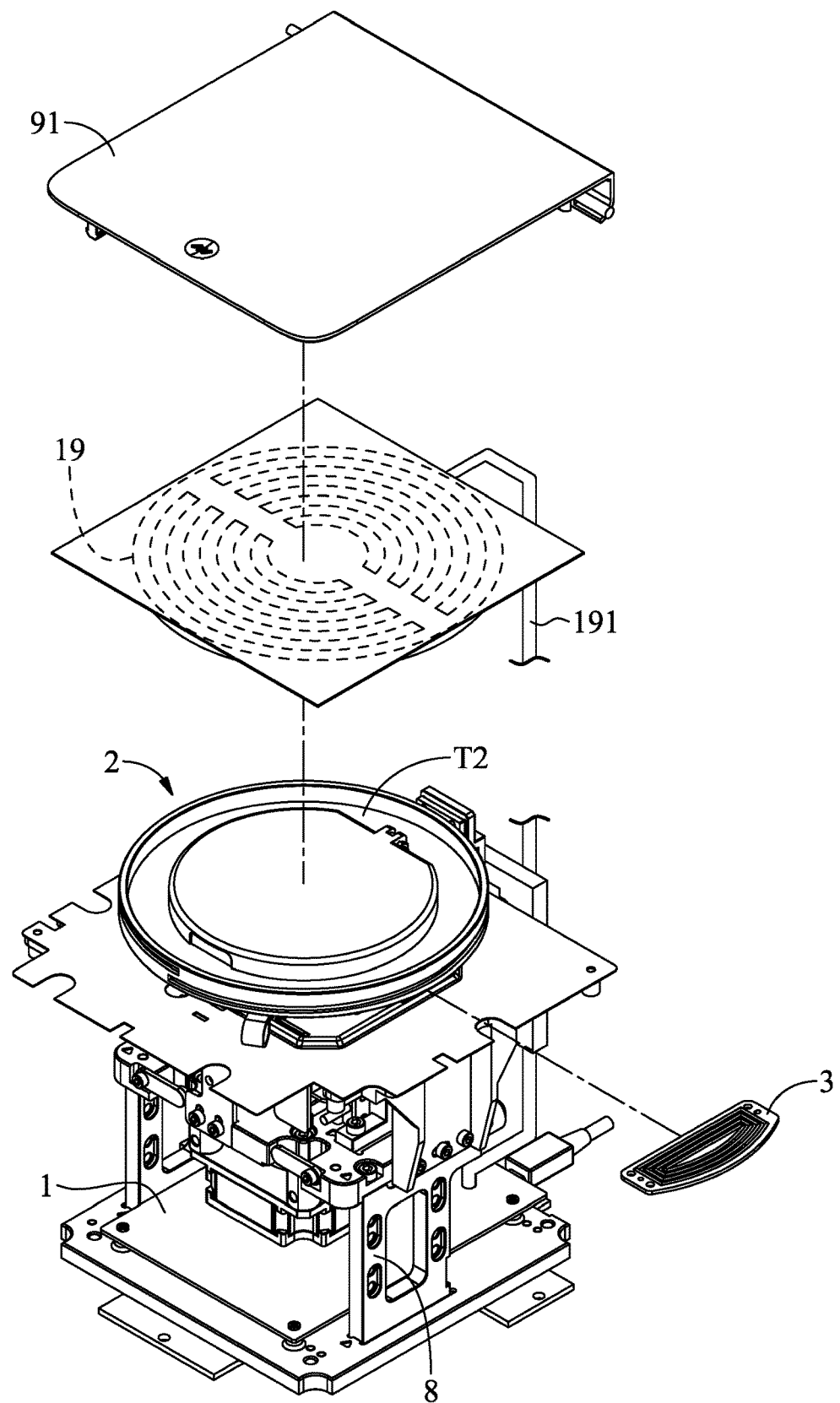
FIG. 5A is a perspective view of a molecular diagnostics apparatus of the first embodiment of the invention.
Figure 5B:
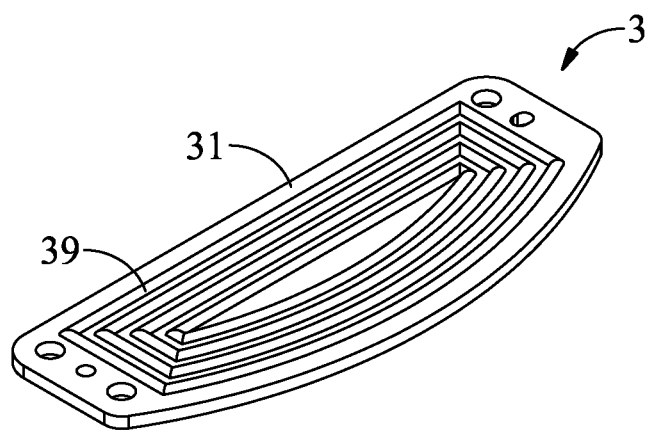
FIG. 5B shows a detection module and a detection module coil of the first embodiment of the invention.

FIG. 5A is a perspective view of the molecular diagnostics apparatus of the first embodiment of the invention. FIG. 5B shows the detection module and the detection module coil of the first embodiment of the invention. With reference to FIGS. 5A and 5B, in one embodiment, the molecular diagnostics apparatus is adapted to perform DNA chain replication to one sample. The molecular diagnostics apparatus includes a bracket 8, a central control module 1, a central control module coil 19, a rotational carrier 2, a detection module 3 and a detection module coil 39. The central control module 1 is disposed on the bracket 8. The central control module coil 19 is coupled to the central control module 1. The rotational carrier 2 is adapted to be rotated relative to the bracket 8. The sample (in test tube) is disposed on the rotational carrier 2. The detection module 3 is disposed on the rotational carrier 2. The detection module coil 39 is coupled to the detection module 3. In a charging mode, the central control module 1 makes the central control module coil 19 provide an induced electromotive force (electromagnetic field). The detection module coil 39 generates an induced current according to the induced electromotive force (electromagnetic field), and the induced current is supplied to the detection module 3.

With reference to FIGS. 2A and 2B, the rotational carrier 2 includes said heating block T1, said holder T2 and said cover T3.

With reference to FIG. 5A, in one embodiment, the molecular diagnostics apparatus further comprises an apparatus cover 91 and a transmission cable 191. The central control module coil 19 is disposed on the apparatus cover 91. The transmission cable 191 connects the central control module coil 19 to the central control module 1.

With reference to FIGS. 2A and 2B, in one embodiment, the molecular diagnostics apparatus further comprises a temperature control module (including said thermoelectric cooling chip T4, said heater T5, said heat sink T6, said fan duct T71 and said fan T72). The temperature control module is adapted to control a temperature (rise and fall) of the rotational carrier. The detection module 3 is a temperature detection module. The detection module 3 detects the temperature of the rotational carrier 2 and generates a temperature data.

With reference to FIGS. 2A and 2B, in one embodiment, the rotational carrier 2 comprises a plurality of receiving recesses 21 (disposed on the heating block T1). The receiving recesses 21 are annular arranged around an axis 201 of the rotational carrier 2. The sample is adapted to be disposed in one of the receiving recesses 21.

Figure 5C:
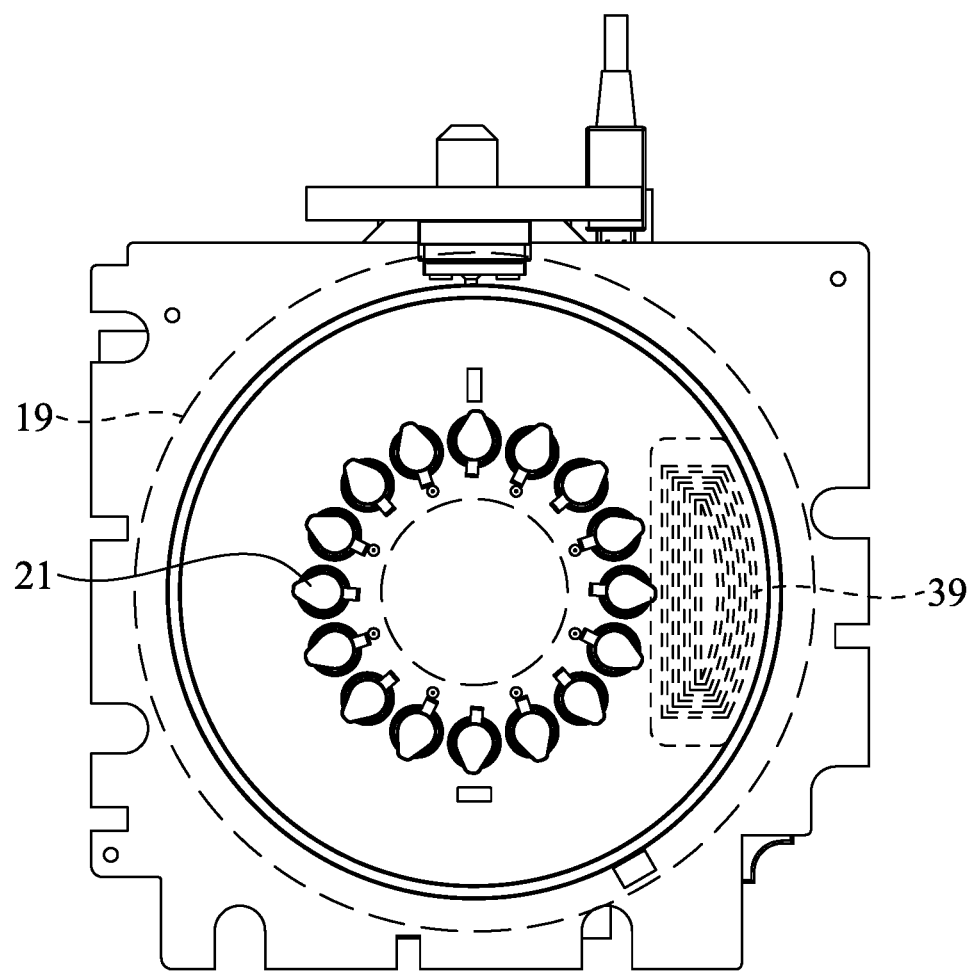
FIG. 5C is a top view of a molecular diagnostics apparatus of the first embodiment of the invention.

FIG. 5C is a top view of the molecular diagnostics apparatus of the first embodiment of the invention. With reference to FIGS. 5A and 5C, in one embodiment, the detection module 3 is disposed on the holder T2. In a vertical projection plane, the detection module 3 is located on an outer side of the receiving recesses 21.

With reference to FIGS. 5A, 5B and 5C, in one embodiment, the detection module 3 comprises a detection module substrate 31. The detection module coil 39 is disposed on the detection module substrate 31. In the vertical projection plane, the detection module coil 39 overlaps with the central control module coil 19. In the embodiment, the central control module coil 19 transfers electric power to the detection module coil 39 through magnetic induction.

Figure 6A:
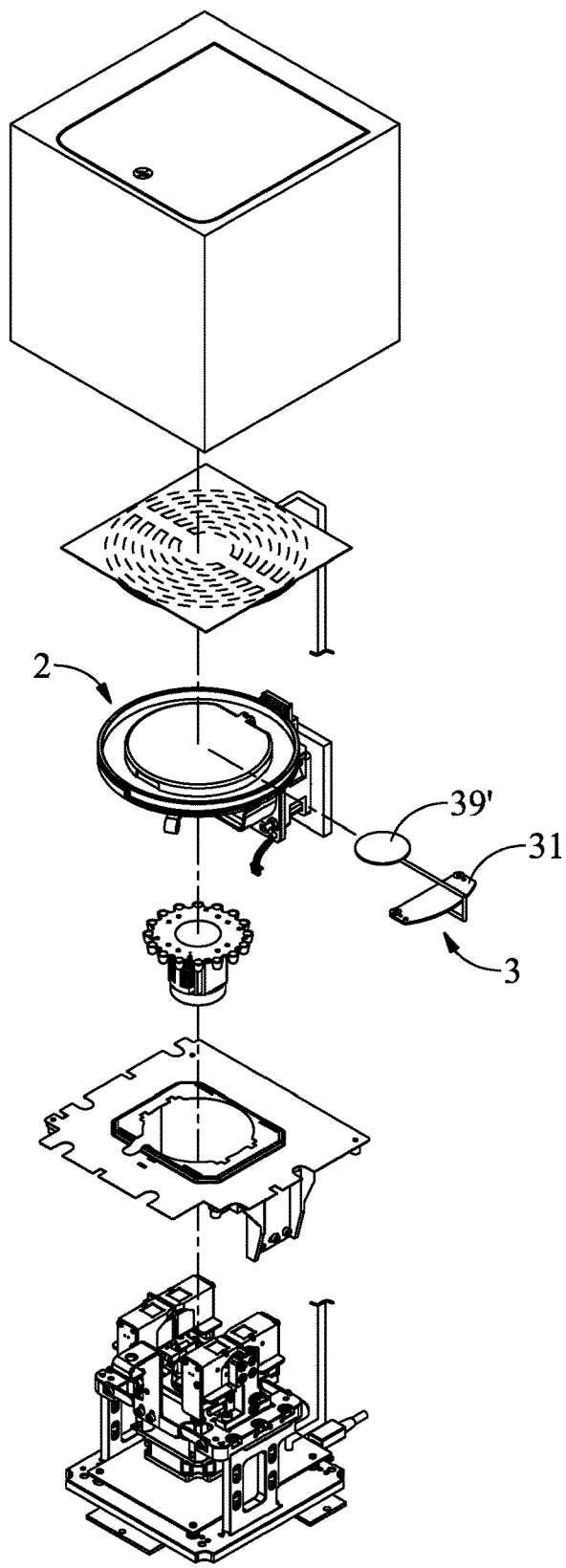
FIGS. 6A and 6B show a molecular diagnostics apparatus of the second embodiment of the invention.
Figure 6B:
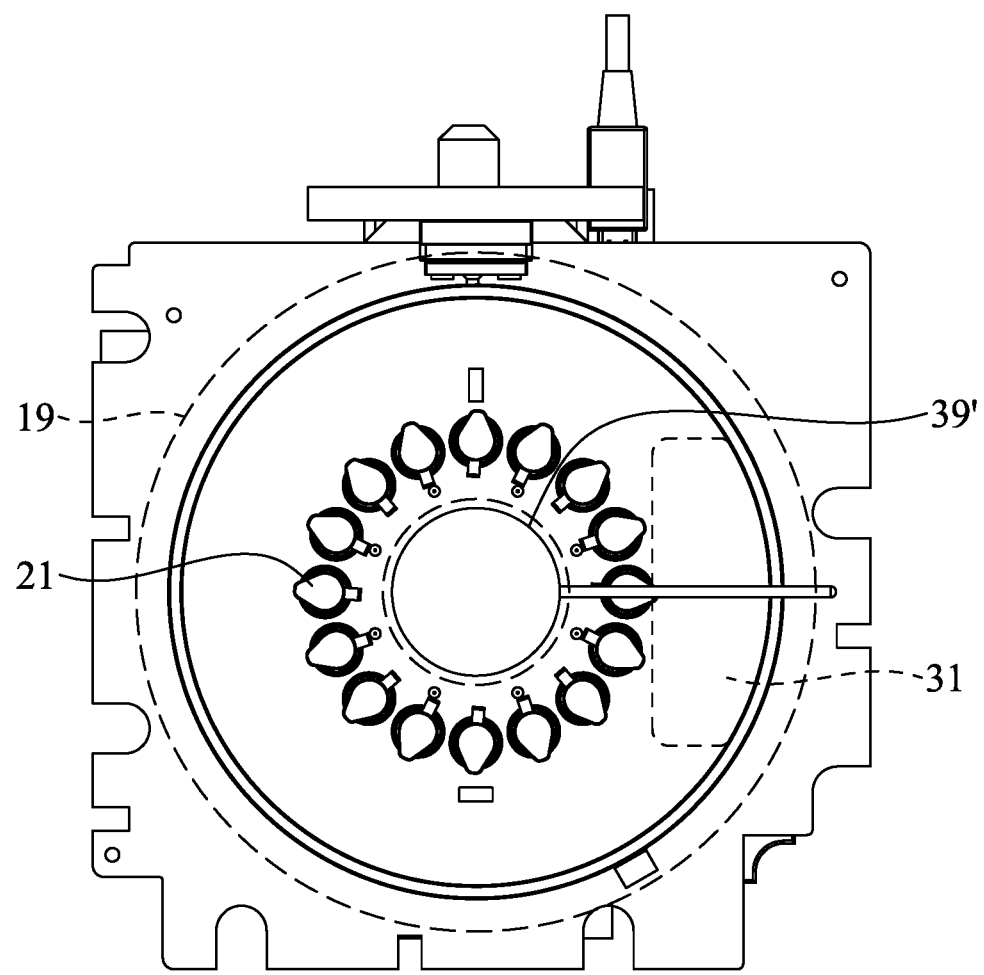

FIGS. 6A and 6B show the molecular diagnostics apparatus of the second embodiment of the invention. With reference to FIGS. 6A and 6B, in this embodiment, the detection module coil 39' is disposed on the rotational carrier 2 and is located on an inner side of the receiving recesses 21. In the vertical projection plane, the detection module coil 39' is coaxial with the central control module coil 19. In the embodiment, the central control module coil 19 transfers electric power to the detection module coil 39' through magnetic resonance. A resonant frequency of the central control module coil 19 and its matching circuit is the same as a resonant frequency of the detection module coil 39' and its matching circuit. In one embodiment, a distance between the central control module coil 19 and the detection module coil 39' is about 2 cm. In one embodiment, a radius of the central control module coil 19 is about 4.5 cm. A turn of winding of the central control module coil 19 is 3. In one embodiment, a radius of the detection module coil 39' is about 1.5 cm. A turn of winding of the detection module coil 39' is 9. A charging transmission unit 11 of a central control module 1 provides or generates alternating current (300 khz) into the central control module coil 19 for transmitting power to the detection module coil 39', and an induced voltage (250 mV) is generated on the detection module coil 39'. The illustration in the above embodiments of the disclosure is shown for exemplary purpose and does not serve to limit the scope of the disclosure. In another embodiment, an induction frequency of the coil can be enhanced to improve the electromotive force (electromagnetic field).

In one embodiment, the detection module coil 39 and the detection module coil 39' can be utilized on one single molecular diagnostics apparatus. For example, the detection module coil 39' generates the induced current, and the detection module coil 39 transmits data. In the embodiment, the molecular diagnostics apparatus can operate simultaneously in a charging mode and a feedback mode (data receiving mode) or can operate simultaneously in a charging mode and an instruction mode.

Figure 7A:
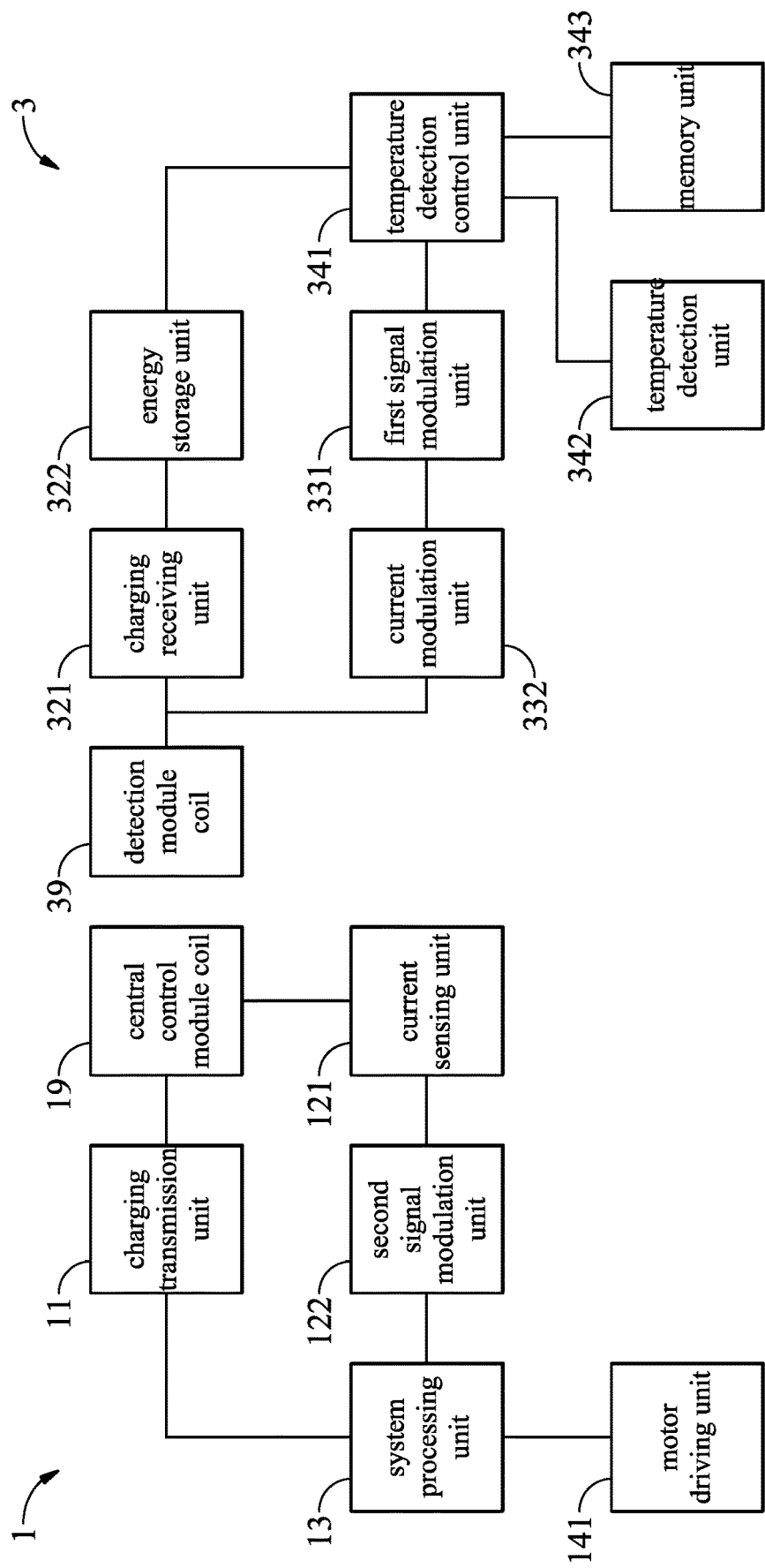
FIG. 7A is a block diagram of a molecular diagnostics apparatus of the third embodiment of the invention.

FIG. 7A is a block diagram of the molecular diagnostics apparatus of the third embodiment of the invention. With reference to FIG. 7A, in one embodiment, the detection module 3 comprises a charging receiving unit 321 (including a rectification unit and a filter), an energy storage unit 322, a first signal modulation unit 331 (including a DAC; Digital to Analog converter), a current modulation unit 332, a temperature detection control unit 341 and a temperature detection unit 342. The current modulation unit 332 is coupled to the detection module coil 39 and the first signal modulation unit 331. The temperature detection control unit 341 is coupled to the temperature detection unit 342 and the first signal modulation unit 331. The central control module 1 comprises a charging transmission unit 11, a current sensing unit 121, a second signal modulation unit 122 (including an ADC; Analog to digital converter) and a system processing unit 13 (including a MCU; Memory Control Unit). The system processing unit 13 is coupled to the charging transmission unit 11 and the second signal modulation unit 122. The current sensing unit 121 is coupled to the second signal modulation unit 122 and the central control module coil 19. The charging transmission unit 11 is adapted to provide or generate high frequency alternating current into the central control module coil 19. The charging transmission unit 11 may include a driving circuit and a drive coil or a driving circuit only. The second signal modulation unit 122 can include an ADC (Analog to digital converter) to receive a signal and output a digital data to the second signal modulation unit 122.

Figure 7B:
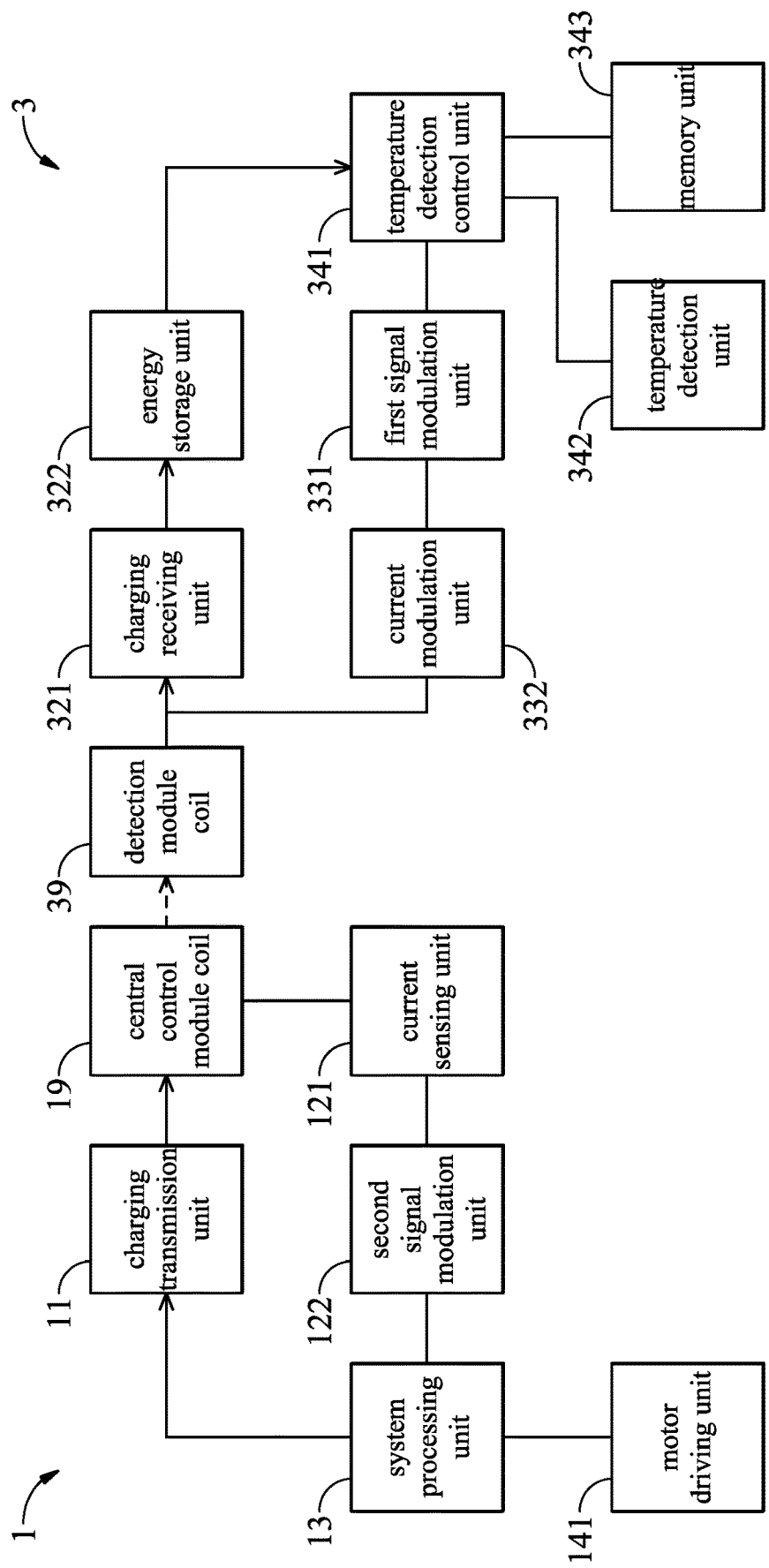
FIG. 7B is a block diagram of the molecular diagnostics apparatus of the third embodiment of the invention, wherein the molecular diagnostics apparatus is in a charging mode.

FIG. 7B is a block diagram of the molecular diagnostics apparatus of the third embodiment of the invention, and the molecular diagnostics apparatus is in a charging mode. With reference to FIG. 7B, in the charging mode, the central control module coil 19 works as a transmitting coil, and the detection module coil 39 works as a receiving coil. The charging transmission unit 11 makes the central control module coil 19 to provide the induced electromotive force (electromagnetic field). The detection module coil 39 generates the induced current according to the induced electromotive force (electromagnetic field). The charging receiving unit 321 charges the energy storage unit 322 with the induced current and supplies power to the detection module 3. In one embodiment, the central control module coil 19 transfer electric power to the detection module coil 39 through magnetic induction. In another embodiment, the central control module coil 19 transfer electric power to the detection module coil 39' through magnetic resonance. A resonant frequency of the central control module coil 19 and associated matching circuit in the charging transmission unit 11 are the same as a resonant frequency of the detection module coil 39' and associated matching circuit in the charging receiving unit 321.

Figure 7C:
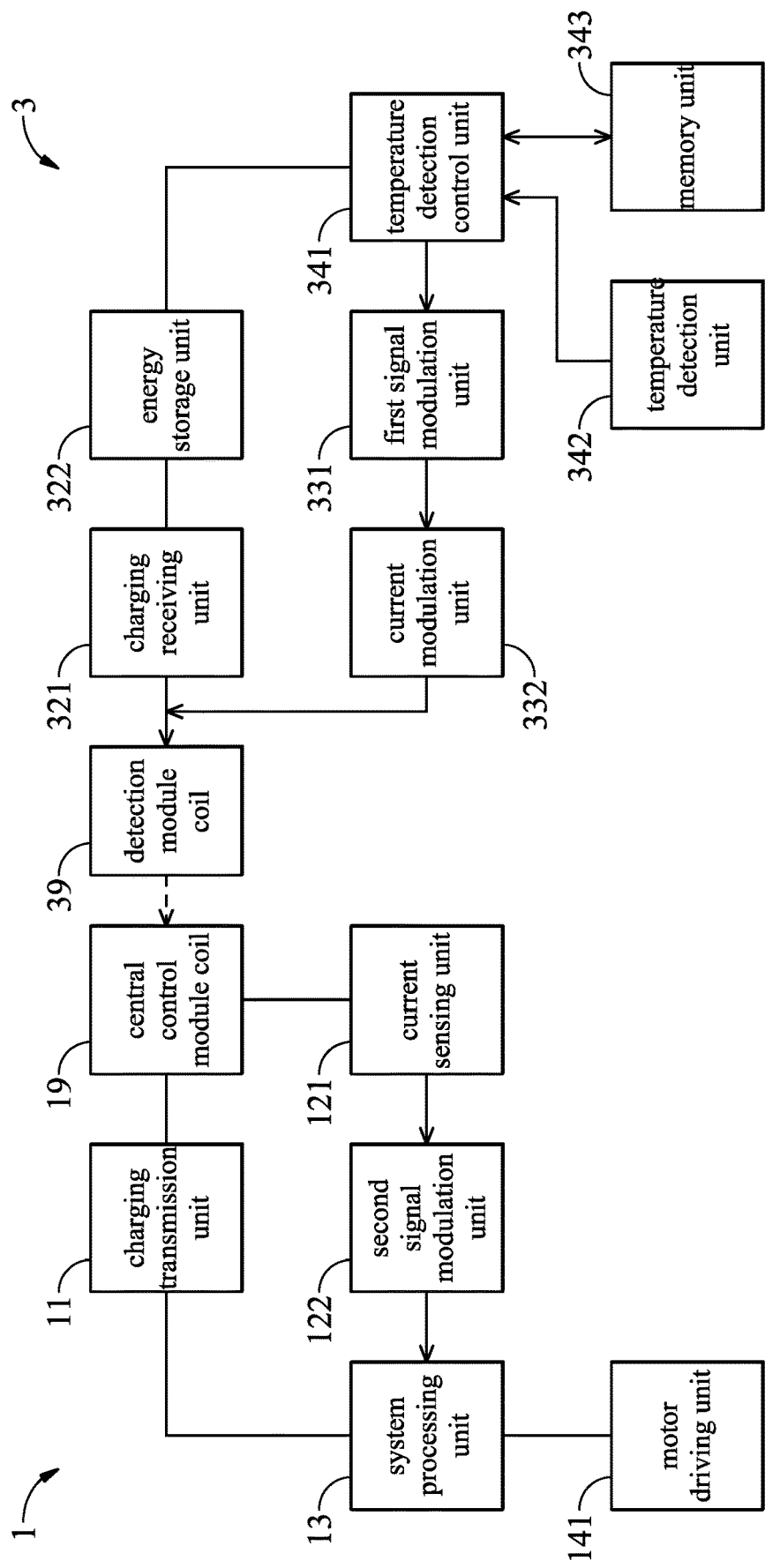
FIG. 7C is a block diagram of the molecular diagnostics apparatus of the third embodiment of the invention, wherein the molecular diagnostics apparatus is in a feedback mode.

FIG. 7C is a block diagram of the molecular diagnostics apparatus of the third embodiment of the invention, and the molecular diagnostics apparatus is in a feedback mode. With reference to FIG. 7C, in the feedback mode (data receiving mode), the temperature detection unit 342 detects the temperature of the rotational carrier 2 and generates the temperature data. The detection module 3 sends the temperature data to the central control module 1 through ways such as electromagnetic induction or modulating an impedance or a loading of the detection module coil 39. The first signal modulation unit 331 and the current modulation unit 332 corporate as a data transmitter, and the current sensing unit 121 and the second signal modulation unit 122 corporate as a data receiver. More specifically, the temperature detection control unit 341 sends the temperature data to the first signal modulation unit 331. The first signal modulation unit 331 switches the current modulation unit 332 or modulates an impedance or a loading of the current modulation unit 332 according to the temperature data to change the output of the induced current and the detection module coil 39 therefore generates a magnetic field variation. The current sensing unit 121 (such as its sensing amplifier) detects a current sensing signal generated by the magnetic field variation detected by the central control module coil 19. The second signal modulation unit 122 (such as its Analog to digital converter, ADC) changes the current sensing signal to a digital signal and sends the digital signal to the system processing unit 13.

In one embodiment, the detection module 3 processes the temperature data to generate a first digital data in a format of Start-Data-End. More specifically, using a 50 degree as an example, the first digital data is 1001100100. The first bit "1" represents start bit, the binary data of 50 degrees is represented as "00110010", and the last bit "0" represents end bit.

In another embodiment, the detection module 3 processes the temperature data to generate a second digital data. The second digital data includes a first sub-data, a second sub-data and a third sub-data in time sequence. The first sub-data may represent timestamp information, data format, and/or identification (ID) such as a header, starting bit or time stamp. The second sub-data may represent payload data such as temperature or feedback command/instruction. The third sub-data may represent parity check bit (such as CRC; Cyclic Redundancy Check), align bit and/or end bit, ect.

In another embodiment, the sensing amplifier of the current sensing unit 121 detects the induced electromotive force (electromagnetic field)/induced voltage on the central control module coil 19, the second signal modulation unit 122 converts the induced electromotive force (electromagnetic field)/induced voltage into a digital signal and outputs the digital signal to the system processing unit 13.

With reference to FIGS. 7A, 7B and 7C, in one embodiment, the detection module 3 further comprises a memory unit 343. The temperature data is stored in the memory unit 343. The temperature detection control unit 341 reads the temperature data from the memory unit 343 and sends the temperature data to the first signal modulation unit 331.

Figure 7D:
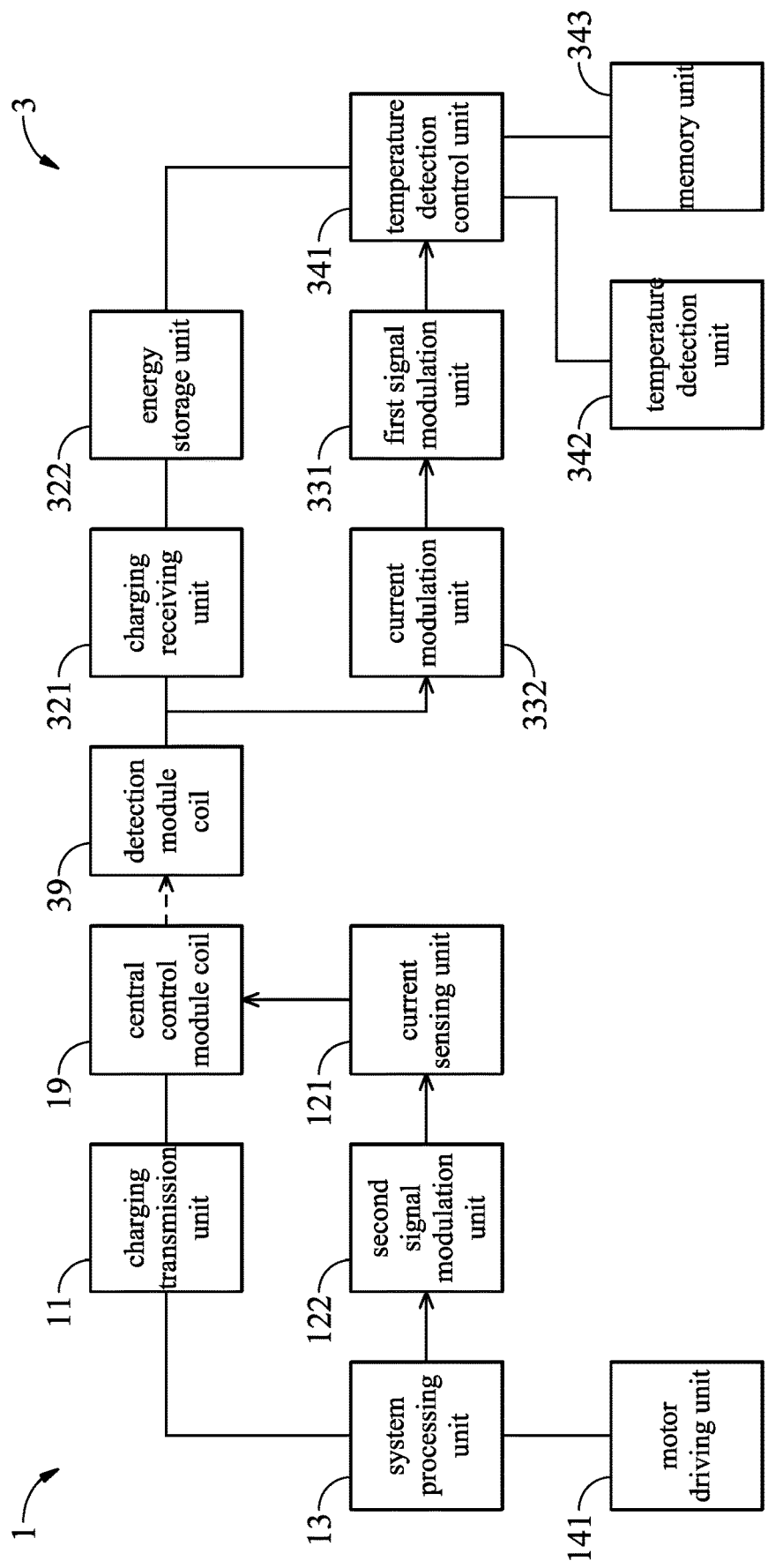
FIG. 7D is a block diagram of the molecular diagnostics apparatus of the third embodiment of the invention, wherein the molecular diagnostics apparatus is in an instruction mode.

FIG. 7D is a block diagram of the molecular diagnostics apparatus of the third embodiment of the invention, and the molecular diagnostics apparatus is in an instruction mode. With reference to FIG. 7D, in the third embodiment of the invention, similar to the signal modulation principle of the feedback mode, in the instruction mode, the system processing unit 13 controls the temperature detection control unit 341 to enter the feedback mode via the central control module coil 19 and the detection module coil 39. In the embodiment, the current sensing unit 121 and the second signal modulation unit 122 corporate as a data transmitter, and the first signal modulation unit 331 and the current modulation unit 332 corporate as a data receiver.

With reference to FIGS. 4 and 7A, in one embodiment, the molecular diagnostics apparatus further comprises said motor R1, and the motor R1 rotates the rotational carrier (and the detection module 3 simultaneously). The central control module 1 further comprises a motor driving unit 141. The motor driving unit 141 is coupled to the motor R1 and the system processing unit 13.

Figure 8A:
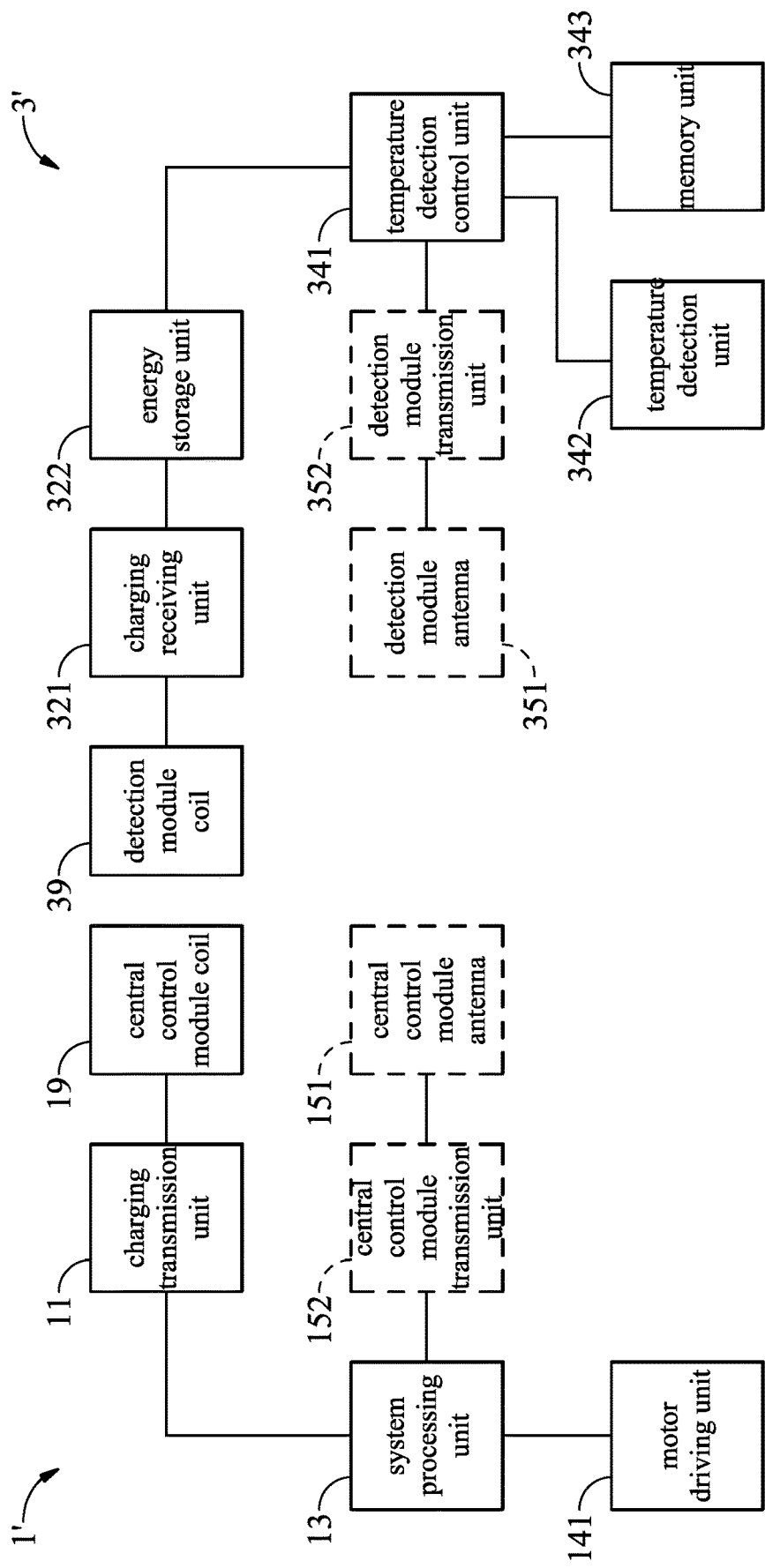
FIG. 8A is a block diagram of a molecular diagnostics apparatus of the fourth embodiment of the invention.

FIG. 8A is a block diagram of the molecular diagnostics apparatus of the fourth embodiment of the invention. With reference to FIG. 8A, in one embodiment, the detection module 3' comprises a charging receiving unit 321, an energy storage unit 322, a detection module antenna 351, a detection module transmission unit 352, a temperature detection control unit 341 and a temperature detection unit 342. The detection module antenna 351 is coupled to the detection module transmission unit 352. The temperature detection control unit 341 is coupled to the detection module transmission unit 352 and the temperature detection unit 342. The central control module 1' comprises a charging transmission unit 11, a central control module antenna 151, a central control module transmission unit 152 and a system processing unit 13. The system processing unit 13 is coupled to the charging transmission unit 11 and the central control module transmission unit 152. The central control module antenna 151 is coupled to the central control module transmission unit 152.

Figure 8B:
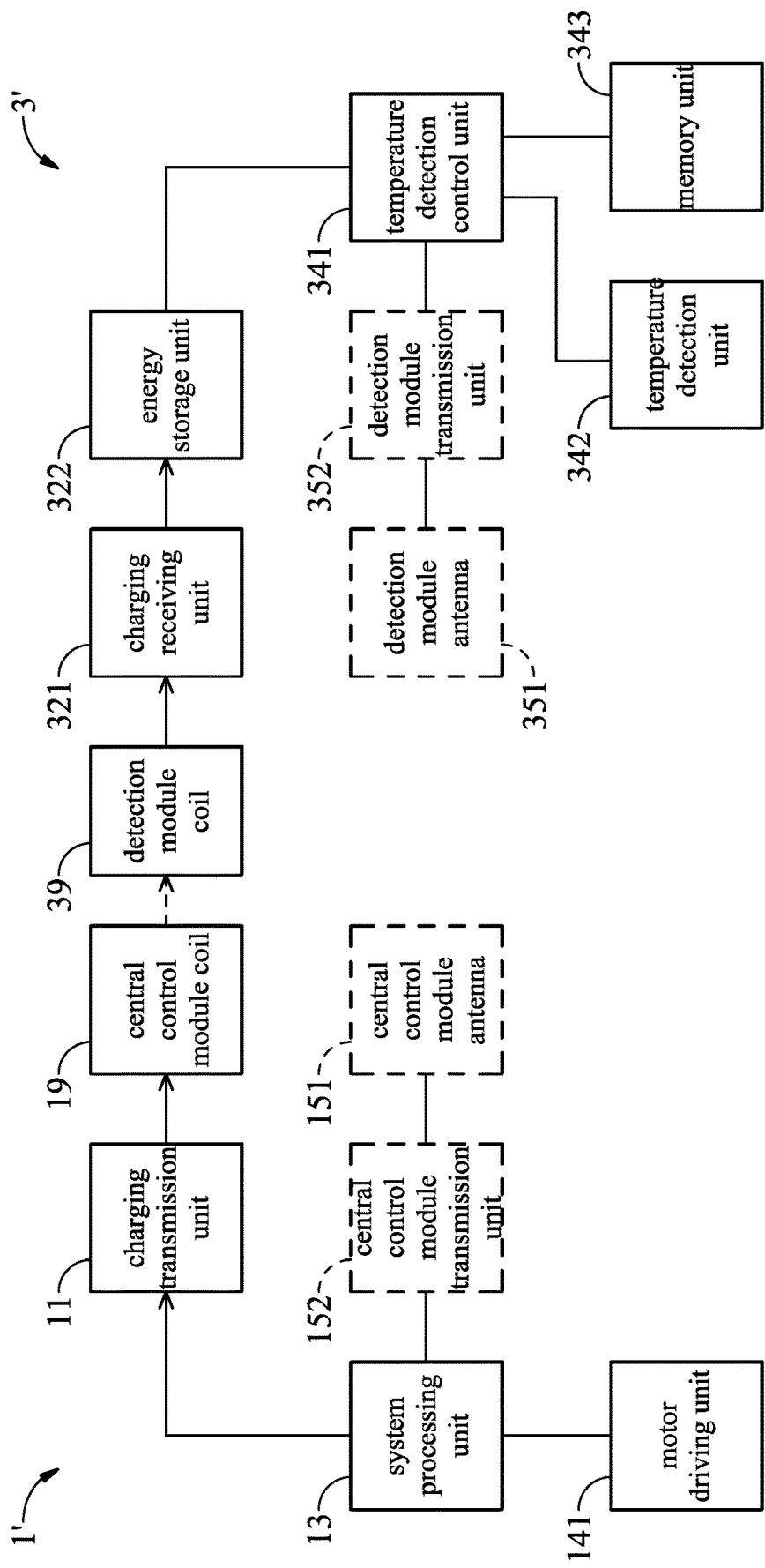
FIG. 8B is a block diagram of the molecular diagnostics apparatus of the fourth embodiment of the invention, wherein the molecular diagnostics apparatus is in a charging mode.

FIG. 8B is a block diagram of the molecular diagnostics apparatus of the fourth embodiment of the invention, and the molecular diagnostics apparatus is in a charging mode. With reference to FIG. 8B, in the charging mode, the charging transmission unit 11 makes the central control module coil 19 to provide the induced electromotive force (electromagnetic field). The detection module coil 39 generates the induced current according to the induced electromotive force (electromagnetic field), the charging receiving unit 321 charges the energy storage unit 322 with the induced current and supplies power to the detection module 3'.

Figure 8C:
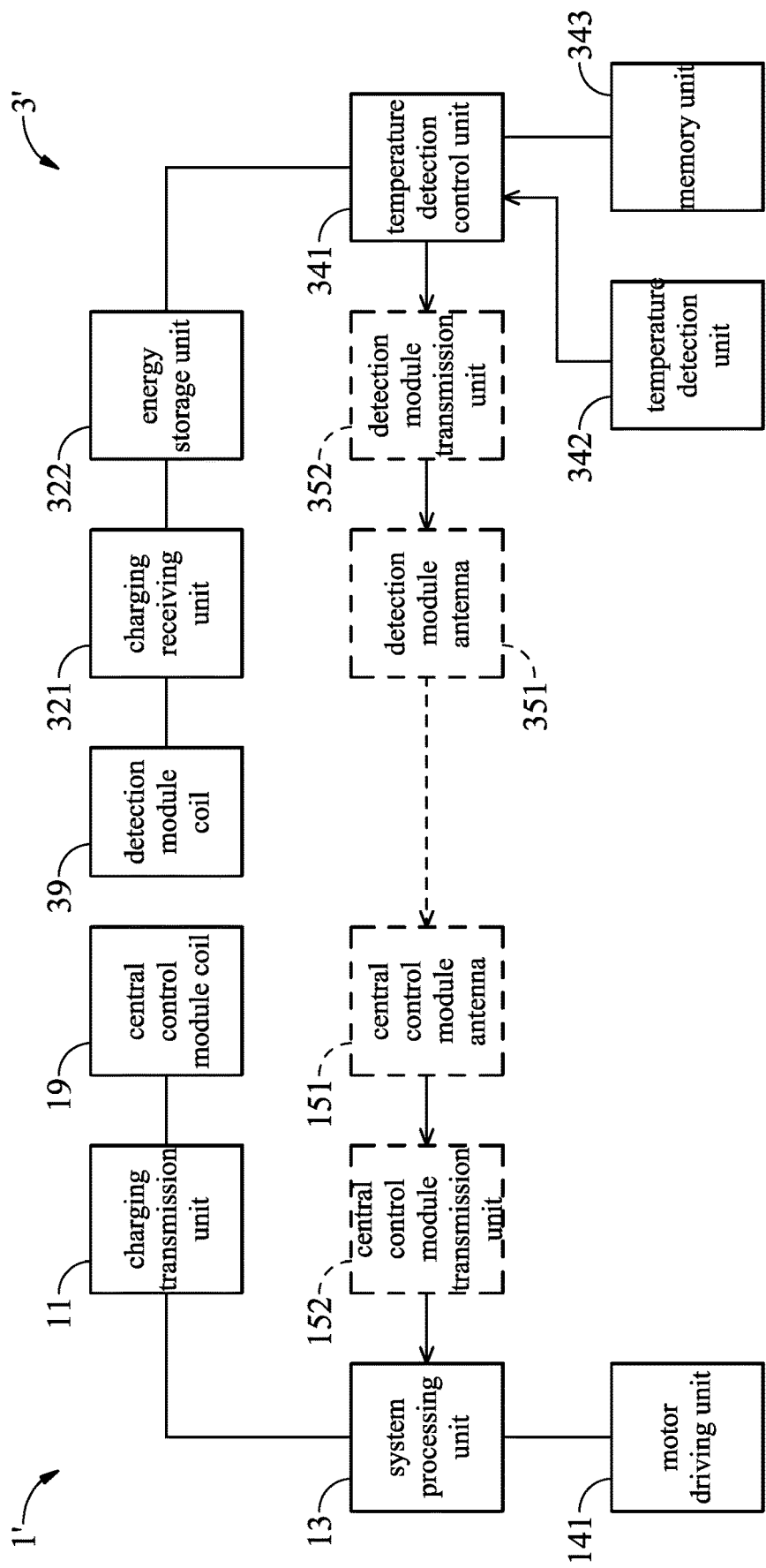
FIG. 8C is a block diagram of the molecular diagnostics apparatus of the fourth embodiment of the invention, wherein the molecular diagnostics apparatus is in a feedback mode.

FIG. 8C is a block diagram of the molecular diagnostics apparatus of the fourth embodiment of the invention, and the molecular diagnostics apparatus is in a feedback mode. With reference to FIG. 8C, in the feedback mode, the temperature detection unit 342 detects the temperature of the rotational carrier 2 and generates the temperature data. The temperature detection control unit 341 sends the temperature data to the detection module transmission unit 352. The detection module transmission unit 352 sends the temperature data via the detection module antenna 351. The central control module transmission unit 152 receives the temperature data sent from the detection module antenna 351 via the central control module antenna 151. The central control module transmission unit 152 transmits the temperature data to the system processing unit 13.

Figure 8D:
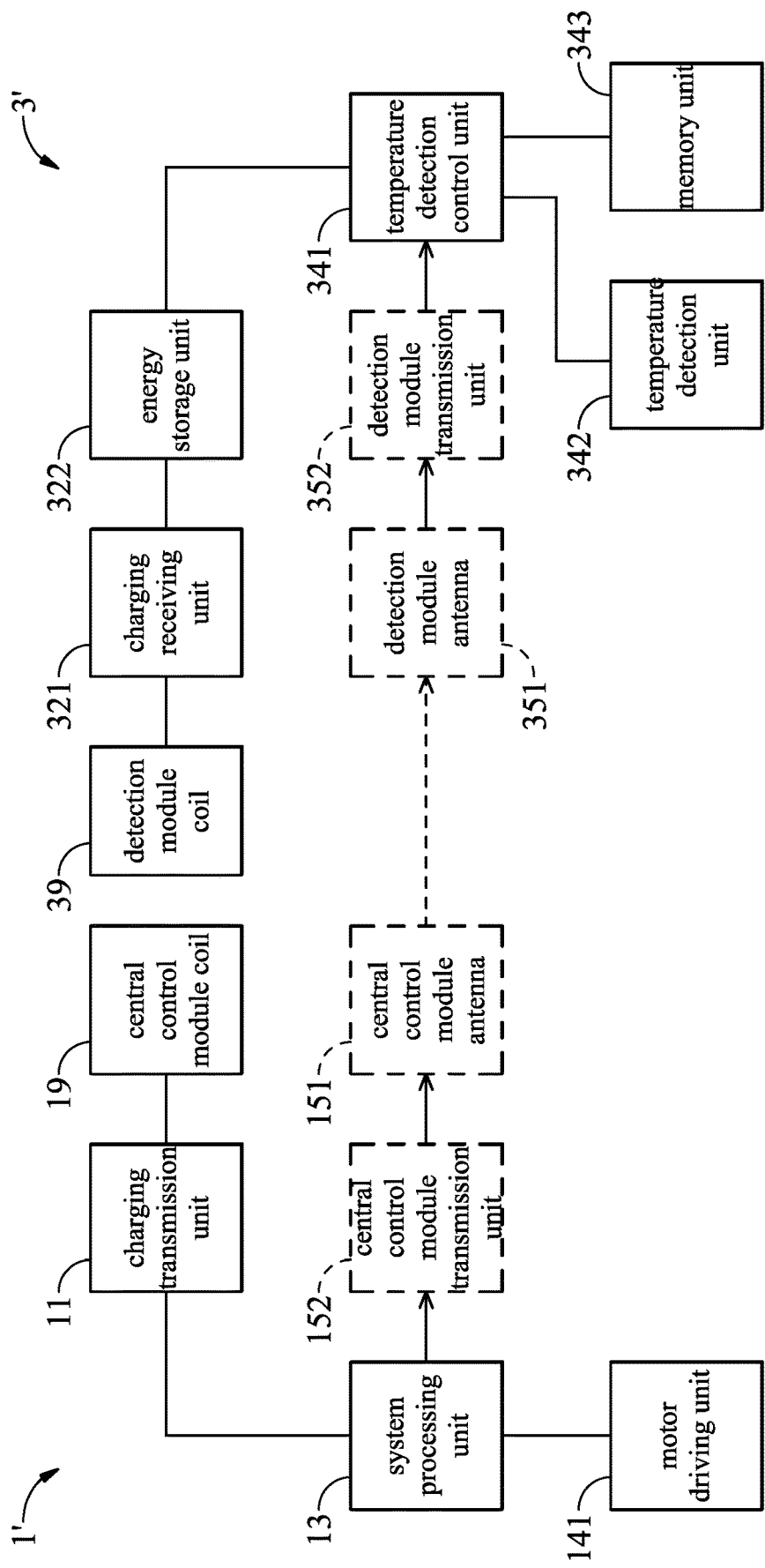
FIG. 8D is a block diagram of the molecular diagnostics apparatus of the fourth embodiment of the invention, wherein the molecular diagnostics apparatus is in an instruction mode.

FIG. 8D is a block diagram of the molecular diagnostics apparatus of the fourth embodiment of the invention, and the molecular diagnostics apparatus is in an instruction mode. With reference to FIG. 8D, in the fourth embodiment of the invention, in the instruction mode, the system processing unit 13 controls the temperature detection control unit 341 to enter the feedback mode via the central control module antenna 151 and the detection module antenna 351.

In the fourth embodiment of the invention, the central control module antenna 151 and the detection module antenna 351 can be Bluetooth antennas or antennas of other communication specifications.

Figure 9:
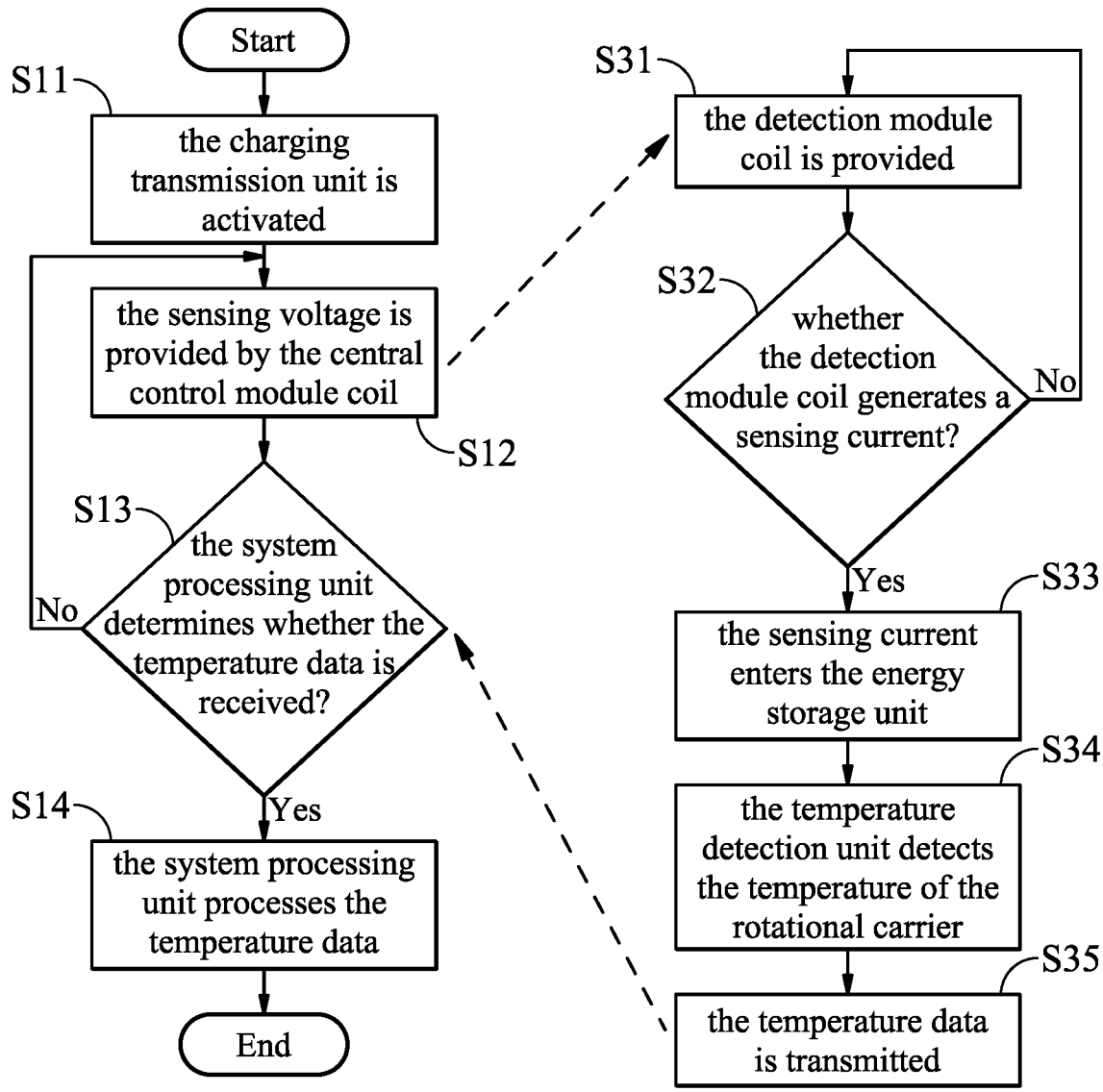
FIG. 9 is a flowchart showing the control process of a molecular diagnostics apparatus of the embodiment of the invention.

FIG. 9 is a flowchart showing the control process of the molecular diagnostics apparatus of the embodiment of the invention. With reference to FIG. 9, as to the central control module, first, the charging transmission unit is activated (S11). Next, the induced electromotive force (electromagnetic field) is provided by the central control module coil (S12). Then, the system processing unit determines whether the temperature data is received (S13). If temperature data is not received, the molecular diagnostics apparatus backs to step S12. If temperature data has been received, the system processing unit processes the temperature data (S14). As to the detection module, first, the detection module coil is provided (S31). Then, when the detection module coil generates an induced current (S32), the induced current enters the energy storage unit (S33). If the detection module coil does not generate the induced current, the detection module keep waits for charging. After the energy storage unit is charged, the temperature detection unit detects the temperature of the rotational carrier (S34). Finally, the temperature data is transmitted (S35).

Utilizing the molecular diagnostics apparatus of the embodiment of the invention, the structure of the molecular diagnostics apparatus can be simplified by the wireless power supply design and the wireless data transmission design. The reliability of the signal transmission and power transmission can be improved.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term).

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A molecular diagnostics apparatus, adapted to perform DNA chain replication to one sample, comprising:
   a bracket;
   a central control module, disposed on the bracket;
   a central control module coil, coupled to the central control module;
   a rotational carrier, adapted to be rotated relative to the bracket, wherein the sample is disposed on the rotational carrier;
   a detection module, disposed on the rotational carrier;
   a detection module coil, coupled to the detection module, wherein in a charging mode, the central control module makes the central control module coil provide an induced electromotive force, the detection module coil generates an induced current according to the induced electromotive force, and the induced current is supplied to the detection module.

2. The molecular diagnostics apparatus as claimed in claim 1, further comprising an apparatus cover and a transmission cable, the central control module coil is disposed on the apparatus cover, and the transmission cable connects the central control module coil to the central control module.

3. The molecular diagnostics apparatus as claimed in claim 1, further comprising a temperature control module, wherein the temperature control module is adapted to control a temperature of the rotational carrier, the detection module is a temperature detection module, and the detection module detects the temperature of the rotational carrier and generates a temperature data.

4. The molecular diagnostics apparatus as claimed in claim 3, wherein the rotational carrier comprises a plurality of receiving recesses, the receiving recesses are annular arranged around an axis of the rotational carrier, and the sample is adapted to be disposed in one of the receiving recesses.

5. The molecular diagnostics apparatus as claimed in claim 4, wherein the rotational carrier further comprises a holder, the detection module is disposed on the holder, and in a vertical projection plane, the detection module is located on an outer side of the receiving recesses.

6. The molecular diagnostics apparatus as claimed in claim 5, wherein the detection module comprises a detection module substrate, the detection module coil is disposed on the detection module substrate, and in the vertical projection plane, the detection module coil overlaps with the central control module coil.

7. The molecular diagnostics apparatus as claimed in claim 5, wherein the detection module coil is disposed on the rotational carrier, the detection module coil is located on an inner side of the receiving recesses, and in the vertical projection plane, the detection module coil is coaxial with the central control module coil.

8. The molecular diagnostics apparatus as claimed in claim 3, wherein the detection module comprises a charging receiving unit, an energy storage unit, a first signal modulation unit, a current modulation unit, a temperature detection control unit and a temperature detection unit, wherein the current modulation unit is coupled to the detection module coil and the first signal modulation unit, and the temperature detection control unit is coupled to the temperature detection unit and the first signal modulation unit, wherein in the charging mode, the detection module coil generates the induced current according to the induced electromotive force, the charging receiving unit charges the energy storage unit with the induced current and supplies power to the detection module, in a feedback mode, the temperature detection unit detects the temperature of the rotational carrier and generates the temperature data, the temperature detection control unit sends the temperature data to the first signal modulation unit, the first signal modulation unit switches the current modulation unit according to the temperature data, and the detection module coil therefore generates a magnetic field variation.

9. The molecular diagnostics apparatus as claimed in claim 8, wherein the central control module comprises a charging transmission unit, a current sensing unit, a second signal modulation unit and a system processing unit, the system processing unit is coupled to the charging transmission unit and the second signal modulation unit, the current sensing unit is coupled to the second signal modulation unit and the central control module coil, wherein in the charging mode, the charging transmission unit makes the central control module coil provide the induced electromotive force, wherein in the feedback mode, the current sensing unit detects a current sensing signal generated by the magnetic field variation detected by the central control module coil, and the second signal modulation unit changes the current sensing signal to a digital signal and sends the digital signal to the system processing unit.

10. The molecular diagnostics apparatus as claimed in claim 9, wherein the detection module further comprises a memory unit, the temperature data is stored in the memory unit, and the temperature detection control unit reads the temperature data from the memory unit and sends the temperature data to the first signal modulation unit.

11. The molecular diagnostics apparatus as claimed in claim 9, further comprising a motor, wherein the motor rotates the rotational carrier, the central control module further comprises a motor driving unit, and the motor driving unit is coupled to the motor and the system processing unit.

12. The molecular diagnostics apparatus as claimed in claim 3, wherein the detection module comprises a charging receiving unit, an energy storage unit, a detection module antenna, a detection module transmission unit, a temperature detection control unit and a temperature detection unit, the detection module antenna is coupled to the detection module transmission unit, the temperature detection control unit is coupled to the detection module transmission unit and the temperature detection unit, wherein in the charging mode, the detection module coil generates the induced current according to the induced electromotive force, the charging receiving unit charges the energy storage unit with the induced current and supplies power to the detection module, in a feedback mode, the temperature detection unit detects the temperature of the rotational carrier and generates the temperature data, the temperature detection control unit sends the temperature data to the detection module transmission unit, and the detection module transmission unit sends the temperature data via the detection module antenna.

13. The molecular diagnostics apparatus as claimed in claim 12, wherein the central control module comprises a charging transmission unit, a central control module antenna, a central control module transmission unit and a system processing unit, the system processing unit is coupled to the charging transmission unit and the central control module transmission unit, the central control module antenna is coupled to the central control module transmission unit, wherein in the charging mode, the charging transmission unit makes the central control module coil provide the induced electromotive force, wherein in the feedback mode, the central control module transmission unit receives the temperature data sent from the detection module antenna via the central control module antenna, and the central control module transmission unit transmits the temperature data to the system processing unit.

14. The molecular diagnostics apparatus as claimed in claim 13, wherein the detection module further comprises a memory unit, the temperature data is stored in the memory unit, and the temperature detection control unit reads the temperature data from the memory unit and sends the temperature data to the detection module transmission unit.

15. The molecular diagnostics apparatus as claimed in claim 13, further comprising a motor, wherein the motor rotates the rotational carrier, the central control module further comprises a motor driving unit, and the motor driving unit is coupled to the motor and the system processing unit.

* * * * *